United States Patent
Levy et al.

(10) Patent No.: US 9,539,339 B2
(45) Date of Patent: Jan. 10, 2017

(54) AFFINITY PEPTIDE-MODIFIED PARTICLES AND TARGETED DRUG DELIVERY METHODS

(71) Applicant: The Children's Hospital of Philadelphia, Philadelphia, PA (US)

(72) Inventors: Robert J. Levy, Merion Station, PA (US); Michael Chorny, Huntingdon Valley, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 14/437,113

(22) PCT Filed: Oct. 25, 2013

(86) PCT No.: PCT/US2013/066858
§ 371 (c)(1),
(2) Date: Apr. 20, 2015

(87) PCT Pub. No.: WO2014/066786
PCT Pub. Date: May 1, 2014

(65) Prior Publication Data
US 2015/0290338 A1    Oct. 15, 2015

Related U.S. Application Data

(60) Provisional application No. 61/718,292, filed on Oct. 25, 2012.

(51) Int. Cl.
| | | |
|---|---|---|
| A61K 38/00 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| C07K 16/00 | (2006.01) | |
| C07K 17/00 | (2006.01) | |
| A61K 9/16 | (2006.01) | |
| A61K 9/50 | (2006.01) | |
| A01N 43/02 | (2006.01) | |
| A61K 31/335 | (2006.01) | |
| A61B 17/52 | (2006.01) | |
| A61N 2/00 | (2006.01) | |
| A61K 47/48 | (2006.01) | |
| A61K 9/00 | (2006.01) | |
| A61K 41/00 | (2006.01) | |
| A61K 31/337 | (2006.01) | |
| A61N 2/02 | (2006.01) | |

(52) U.S. Cl.
CPC ....... *A61K 47/48238* (2013.01); *A61K 9/0009* (2013.01); *A61K 31/337* (2013.01); *A61K 41/00* (2013.01); *A61K 47/4893* (2013.01); *A61K 47/48861* (2013.01); *A61K 47/48915* (2013.01); *A61N 2/002* (2013.01); *A61N 2/02* (2013.01)

(58) Field of Classification Search
CPC ....... C07K 14/745; C07K 14/75; A61K 38/36; A61K 38/363
See application file for complete search history.

(56) References Cited

U.S. PATENT DOCUMENTS

| 8,513,380 | B2 * | 8/2013 | Barker | A61K 47/48292 530/300 |
|---|---|---|---|---|
| 2002/0142046 | A1 | 10/2002 | Yen | |
| 2009/0082611 | A1 | 3/2009 | Levy | |
| 2010/0172835 | A1 | 7/2010 | Ruoslahti et al. | |
| 2010/0260677 | A1 * | 10/2010 | Bhatia | A61K 41/0052 424/9.1 |
| 2010/0260780 | A1 | 10/2010 | Levy | |
| 2011/0076767 | A1 | 3/2011 | Chrony | |

FOREIGN PATENT DOCUMENTS

| GB | WO 2005035002 A1 * | 4/2005 | ............. A61K 38/08 |
|---|---|---|---|
| WO | WO 2004/017907 A2 | 3/2004 | |
| WO | 2005035002 | 4/2005 | |
| WO | WO 2009/052367 A1 | 4/2009 | |
| WO | 2012061193 | 5/2012 | |
| WO | 2012092339 | 7/2012 | |
| WO | WO 2012092339 A2 * | 7/2012 | ....... A61K 47/48107 |

OTHER PUBLICATIONS

Costantini and Zacharski "The role of fibrin in tumor metastasis" Cancer and Metastasis Reviews 11:283-290. Published 1992.*
Chan, J.M. et al., "In vivo prevention of arterial restenosis with paclitaxel-encapsulated targeted lipid-polymeric nanoparticles," Nov. 29, 2011, pp. 19347-19352, vol. 108, No. 48, Proceedings of the National Academy of the Sciences USA.
Chan, J.M. et al., "Spatiotemporal controlled delivery of nanoparticles to injured vasculature," Feb. 2, 2010, pp. 2213-2218, vol. 107, No. 5, Proceedings of the National Academy of the Sciences USA.

(Continued)

*Primary Examiner* — James H Alstrum Acevedo
*Assistant Examiner* — Zachary J Miknis
(74) *Attorney, Agent, or Firm* — RatnerPrestia

(57) ABSTRACT

A therapeutic particle comprises a particle comprising one or more therapeutic agents and one or more fibrin-avid peptide variants attached to the surface of the particle. A method for magnetically targeting a therapeutic agent toward a device in a subject, such as a temporarily introduced magnetizable catheter or an implanted stent, comprises administering the therapeutic particles to the subject and generating a magnetic field, which targets the magnetic particles toward the device. The affinity peptide-modified therapeutic particles may comprise an effective amount of an anti-proliferative agent, such as paclitaxel, to inhibit or prevent in-stent restenosis.

33 Claims, 1 Drawing Sheet

(56) References Cited

OTHER PUBLICATIONS

Chorny, M., et al., "Targeting stents with local delivery of paclitaxel-loaded magnetic nanoparticles using uniform fields," May 4, 2010, pp. 8346-8351, vol. 107, No. 18, Proceedings of the National Academy of the Sciences USA.

International Preliminary Report on Patentability and Written Opinion for International Application No. PCT/US2013/066858 issued Apr. 28, 2015.

International Search Report for International Application No. PCT/US2013/066858 mailed Jan. 31, 2014.

McCarthy, J.R. et al., "Multimodal nanoagents for the detection of intravascular thrombi," 2009, pp. 1251-1255, vol. 20, No. 6, Bioconjugate Chemistry (abstract only).

Communication issued by European Patent Office for European Application No. 13848459.7 on May 23, 2016.

* cited by examiner

AFFINITY PEPTIDE-MODIFIED PARTICLES AND TARGETED DRUG DELIVERY METHODS

CROSS-REFERENCE TO RELATED APPLICATIONS

This application is a U.S. National Phase filing of International Application No. PCT/US2013/066858, filed Oct. 25, 2013, which claims the benefit of priority of U.S. Provisional Application No. 61/718,292, filed Oct. 25, 2012, the entire contents of which applications are incorporated by reference herein, in their entireties and for all purposes.

FIELD OF THE INVENTION

This invention relates generally to targeted drug delivery using therapeutic particles. More specifically, the invention relates to affinity peptide-modified nanoparticles formulated with one or more anti-proliferative agents and targeted to temporarily placed or permanently placed devices.

BACKGROUND OF THE INVENTION

Therapeutic agents delivered in a conventional or non-specific manner, such as by oral dosing or intravenous administration, are often distributed to non-designated areas of the body. As a consequence, the agent may be metabolized, for example, through first pass metabolism of the liver, thereby resulting in diminished bioavailability and the possibility for increased dosing at a higher cost and with the risk of adverse side effects. In addition, non-specific distribution of therapeutic agents may result in adverse effects and unwanted pharmacological responses in the subject to which they are administered. As a result, certain agents may be contraindicated in certain subjects or under certain conditions.

Nanoparticles and microparticles have shown potential as vehicles for the targeted delivery of therapeutic agents, including enzymes for enzyme replacement therapy, hormones, cell modifying agents and genetic material. Attempts to use nanoparticles and microparticles for site-specific delivery have shown potential to lower adverse effects in patients, attributed in part to lower doses of therapeutic agents being required. However, there is a significant unmet medical need for site-specific drug delivery, for example in injured arteries after angioplasty and stenting, that inhibits redistribution of the drug and allows for greater retention of the drug at the injured site.

SUMMARY OF THE INVENTION

An embodiment of the present invention provides a therapeutic particle. The particle may include a nanoparticle or microparticle. Moreover, the particle may be a magnetic nanoparticle (MNP) or a non-magnetic particle. The particle may include one or more therapeutic agents and one or more affinity peptides, namely, fibrin-avid peptide variants.

The one or more fibrin-avid peptide variants may be attached to the surface of the particle. The one or more therapeutic agents may comprise, for example, an anti-proliferative agent, such as paclitaxel. In particular embodiments, one or more crosslinking agents may be attached to the surface of the particle, and one or more cysteinated variants of a fibrin-avid peptide may be attached to the one or more crosslinking agents.

Another embodiment of the present invention provides a method for magnetically targeting a therapeutic agent toward a device in a subject. The device may be a temporarily introduced device, such as a catheter. Alternatively, the device may be an implanted device, such as a stent. The method may include the step of administering therapeutic particles of the present invention to the subject, and generating a magnetic field. The magnetic field may generate a gradient that targets the therapeutic particles toward the device. The therapeutic particles preferably comprise an effective amount of the one or more therapeutic agents to provide an anti-proliferative effect. In stented arteries, for example, the therapeutic particles may comprise an effective amount of the one or more therapeutic agents to inhibit in-stent restenosis.

Another embodiment of the present invention provides a method for making a therapeutic particle comprising attaching one or more fibrin-avid peptide variants to the surface of a particle comprising one or more therapeutic agents. In preferred embodiments, particles are first chemically activated using crosslinking agents that provide thiol reactivity, then reacted with a cysteinated variant of a fibrin-avid peptide.

BRIEF DESCRIPTION OF THE FIGURES

The invention may be further understood by reference to the drawings in which.

DETAILED DESCRIPTION OF EMBODIMENTS OF THE INVENTION

Figure 1:
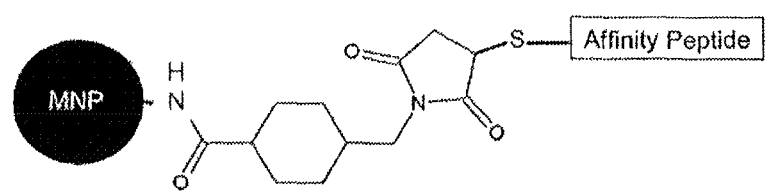
FIG. 1 illustrates an MNP-affinity peptide surface modification strategy according to an embodiment of the present invention. In this embodiment, albumin-coated MNP are first chemically activated using sulfo-SMCC to provide thiol reactivity, then reacted with the affinity peptide having terminal cysteines.

The applicants have developed novel particles formulated with therapeutic agents that exhibit high affinity for injured areas of the body, such as blood vessels. The surface of each particle is modified with an affinity peptide, namely, a fibrin-avid peptide variant. Affinity targeting in accordance with the invention can be applied as a stand-alone strategy or in combination with other strategies like magnetic targeting. Therefore, the term "particles" as used herein, includes both magnetic particles and non-magnetic particles. The term "particles" also includes microparticles and nanoparticles. The particles may include one or more therapeutic agents and one or more affinity peptides, namely, fibrin-avid peptide variants.

Fibrin was chosen as the affinity target as it is generally only present at the site of arterial injury, thus effectively restricting the drug-loaded particles to this region. With this approach, the interaction of therapeutic particles with the injured arterial wall is enhanced, due to the interaction between the affinity peptide on the surface of the particles and the fibrin in the injured arterial wall, thereby extending the retention of the drug-loaded particles at the target site. In particular embodiments, biodegradable particles formulated with antiproliferative agents, and targeted to injured arteries in the presence of a uniform magnetizing field, provide a clinically viable, safe and efficient therapeutic strategy for preventing or inhibiting re-obstruction of the injured arteries after stent angioplasty (i.e., in-stent restenosis).

Angioplasty and stent placement cause tissue trauma. During angioplasty, a balloon is passed across an atherosclerotic plaque in a coronary artery and inflated, compressing the plaque and widening the opening of the artery. Compression typically creates trauma to the blood vessel wall, which in turn leads to deposition of proteinacious matrix containing fibrin. Restenosis, the re-narrowing of a coronary artery due to the formation of obstructed regions at the site of the angioplasty and/or stent placement, is a common occurrence. One mechanism by which restenosis occurs is by thrombosis, or blood clotting, at the site of the treatment. Restenosis can be greatly reduced by using anti-proliferative or "anti-clotting" drugs after the procedure.

In one embodiment, MNPs are formulated with one or more therapeutic agents and surface-modified with a fibrin-avid peptide variant. The surface-modified MNPs enable efficient and site-specific drug delivery to treatment areas when applied in combination with a magnetic field. The improved retention of the drug-load nanoparticles at the injured site, due to surface modification with the fibrin-avid peptide variant, inhibits redistribution of the therapeutic agent(s) from the target site after the magnetic field is removed.

The term "subject" or "patient", used herein, refers to a mammalian subject, such as a human being. The subject may be a human that has an implanted device, such as a stent, or a temporarily introduced device, such as a catheter. Examples of temporarily implantable devices are disclosed, for example, in WO 2012/061193, which is incorporated by reference herein in its entirety.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest, delay the onset of or partially prevent a target disease or condition or one or more symptoms thereof (e.g., in-stent restenosis).

The terms "therapeutic agent," "drug," or "active agent" may be used herein interchangeably to refer to the pharmacologically active compound(s) in the particles. This is in contrast to other ingredients in the particles, such as excipients, which are substantially or completely biologically inactive.

As used herein, a "magnetic nanoparticle" is a nanoparticle that is permanently magnetic or magnetizable upon exposure to an external magnetic field. Magnetic nanoparticles can be manipulated using a magnetic field and typically comprise one or more magnetic elements, such as iron, nickel, and/or cobalt. The magnetic nanoparticles used herein are preferably biodegradable.

An embodiment of the present invention comprises a therapeutic particle comprising or consisting of a magnetic nanoparticle comprising one or more therapeutic agents and one or more affinity peptides, namely, fibrin-avid peptide variants. The fibrin-avid peptide variants are attached to the surface of the magnetic nanoparticle. In preferred embodiments, the one or more therapeutic agents comprise or consist of one or more anti-proliferative agents, such as paclitaxel. The one or more therapeutic agents are preferably encapsulated by the magnetic nanoparticle.

As used herein, a "fibrin-avid peptide variant" is a peptide having a high affinity for fibrin, and preferably comprising the amino acid sequence Gly Pro Arg Pro (SEQ ID NO: 1) (i.e., a shorter core sequence of a fibrin-avid peptide), or comprising the amino acid sequence Gly Pro Arg Pro Pro (SEQ ID NO: 2) (i.e., an extended amino acid sequence of a fibrin-avid peptide). A fibrin-avid peptide variant preferably has an amino acid sequence that includes one or more amino acids in addition to Gly Pro Arg Pro (SEQ ID NO: 1) or Gly Pro Arg Pro Pro (SEQ ID NO: 2). These fibrin-avid peptide variants may have the amino acid sequence Gly Pro Arg Pro Xaa (SEQ ID NO: 3), where Xaa could be between 1 to 50 amino acids, either naturally-occurring or artificial (i.e., Xaa at positions 5-54 may be any naturally-occurring or artificial amino acid and up to 49 of them may be absent); or Gly Pro Arg Pro Pro Xaa (SEQ ID NO: 4), where Xaa could be between 1 to 50 amino acids, either naturally-occurring or artificial (i.e., Xaa at positions 6-55 may be any naturally-occurring or artificial amino acid and up to 49 of them may be absent).

In preferred embodiments, the fibrin-avid peptide variant(s) comprise one or more cysteine residues in addition to Gly Pro Arg Pro (SEQ ID NO: 1) or Gly Pro Arg Pro (SEQ ID NO: 2) (referred to herein as cysteinated variants), most preferably one or more terminal cysteine residues. These fibrin-avid peptide variants may have the amino acid sequence Gly Pro Arg Pro Xaa Cys (SEQ ID NO: 5), where Xaa could be between 0 to 50 amino acids, either naturally-occurring or artificial (i.e., Xaa at positions 5-54 may be any naturally-occurring or artificial amino acid and up to fifty of them may be absent); or Gly Pro Arg Pro Pro Xaa Cys (SEQ ID NO: 6), where Xaa could be between 0 to 50 amino acids, either naturally-occurring or artificial (i.e., Xaa at positions 6-55 may be any naturally-occurring or artificial amino acid and up to fifty of them may be absent). In particular embodiments, the fibrin-avid peptide variants have the amino acid sequence Gly Pro Arg Pro Xaa Cys (SEQ ID NO: 7), where Xaa could be between 1 to 50 Gly residues (i.e., Xaa at positions 5-54 are Gly and up to 49 of them may be absent); or Gly Pro Arg Pro Pro Xaa Cys (SEQ ID NO: 8), where Xaa could be between 1 to 50 Gly residues (i.e., Xaa at positions 6-55 are Gly and up to 49 of them may be absent). In exemplary embodiments, for example, the fibrin-avid peptide variant(s) comprise or consist of the amino acid sequence Gly Pro Arg Pro Pro Gly Gly Gly Cys (SEQ ID NO: 9). According to particular aspects of the invention, the one or more fibrin-avid peptide variants have an amino acid sequence selected from the group consisting of: SEQ ID NO: 3, SEQ ID NO: 4, SEQ ID NO: 5, SEQ ID NO: 6, SEQ ID NO: 7, SEQ ID NO: 8, and SEQ ID NO: 9. The fibrin-avid peptide variants attached to a particle may each have the same amino acid sequence. Alternatively, the amino acid sequences among the fibrin-avid peptide variants attached to a particle may vary. The one or more fibrin-avid peptide variants may be attached to the surface of the particle (e.g., magnetic nanoparticle) either directly or indirectly (e.g., by attachment to a crosslinking agent that is attached to the particle). According to particular embodiments, one or more crosslinking agents are directly attached to the surface of the particle, and the one or more fibrin-avid peptide variants are directly attached to the one or more crosslinking agents. The term "attached" as used herein is interchangeable with the terms "conjugated," "linked" or "bonded." One form of attachment is chemical bonding, such as covalent bonding. The therapeutic particles of the present invention are preferably not adapted for medical imaging; for example, the therapeutic particles preferably do not include an imaging agent, such as a radioactive label (e.g., Technetium-99m), attached to or otherwise associated with the particles.

According to particular embodiments, the magnetic particle is a polylactide-based MNP. The MNP may comprise one or more magnetic elements selected from the group consisting of iron, nickel, cobalt, and combinations thereof. In exemplary embodiments, the MNP comprises magnetite, which is a magnetic iron mineral with the chemical formula $Fe_3O_4$, or $FeO.Fe_2O_3$.

Nanoparticles in accordance with the invention preferably have a diameter of between about 100 nm to about 500 nm, or between about 150 nm to about 350 nm, or between about 200 nm to about 300 nm, or between about 250 nm to about 280 nm. In preferred embodiments, a plurality of the fibrin-avid peptide variants are attached to the surface of the nanoparticle. For example, between about 10,000 to about 90,000, or between about 30,000 to about 50,000 (e.g., about 40,000) of the fibrin-avid peptide variants may be attached to the surface of each nanoparticle.

According to another embodiment of the present invention, a method for magnetically targeting a therapeutic agent toward a device, such as a stent, in a subject (e.g., a method for inhibiting in-stent restenosis in stented arteries) comprises administering therapeutic particles of the present invention (described herein) to the subject, and generating a magnetic field. The magnetic field generates a magnetic field gradient that targets the MNPs toward the device, so that the therapeutic particles can be guided toward the device by the magnetic force. According to one embodiment, the step of generating the magnetic field comprises using a pair of electromagnets to generate a uniform magnetic field. Methods of using magnetization to target MNPs to a desired location are disclosed, for example, in U.S. Publication No. 2009/0082611, U.S. Publication No. 2010/0260780, and U.S. Publication No. 2011/0076767, which are incorporated by reference herein in their entireties. The therapeutic particles preferably comprise a therapeutically effective amount of the one or more therapeutic agents (e.g., an anti-proliferative agent, such as paclitaxel) to provide an anti-proliferative or anti-clotting effect to stented arteries (e.g., to inhibit or prevent the occurrence of in-stent restenosis).

According to another embodiment, a method for making a therapeutic particle of the present invention comprises attaching one or more fibrin-avid peptide variants to the surface of an MNP comprising one or more therapeutic agents. Any method known by those skilled in the art can be used to make the MNPs. For example, an emulsification-solvent evaporation method, may be used to make the MNPs (see, e.g., Chorny, I. Fishbein, B. B. Yellen, I. S. Alferiev, M. Bakay, S. Ganta, R. Adamo, M. Amiji, G. Friedman, and R. J. Levy. Targeting stents with local delivery of paclitaxel-loaded magnetic nanoparticles using uniform fields. *Proc Natl Acad Sci USA* 107: 8346-51 (2010)).

As discussed above, the fibrin-avid peptide variants may be attached to the surface of an MNP either directly or indirectly. Thus, the method may further comprise attaching one or more crosslinking agents to the surface of the MNPs. In preferred embodiments, the MNPs are first chemically activated using crosslinking agent(s), such as a compound having thiol reactive functions (e.g., a compound having thiol reactive maleimido functions, such as sulfo-SMCC), to provide thiol reactivity to the MNP, and then reacted with terminal cysteines of the fibrin-avid peptide variants. Thus, the crosslinking agent(s) become bonded to the MNP, and then the fibrin-avid peptide variants become bonded to the crosslinking agent(s). For example, the MNPs (preferably albumin-stabilized magnetic nanoparticles) may be incubated with a crosslinking agent in order to introduce thiol-reactive (maleimido) groups, which are subsequently reacted with high selectivity with terminal cysteine residues of the fibrin-avid peptide variants. Sulfo-SMCC is also referred to as (Sulfosuccinimidyl-4-N-maleimidomethyl)cyclohexane-1-carboxylate, or 4-9N-Maleimidomethyl)cyclohexane-1-carboxylic acid 3-sulfo-N-hydroxysuccinimide ester sodium.

Figure 2:
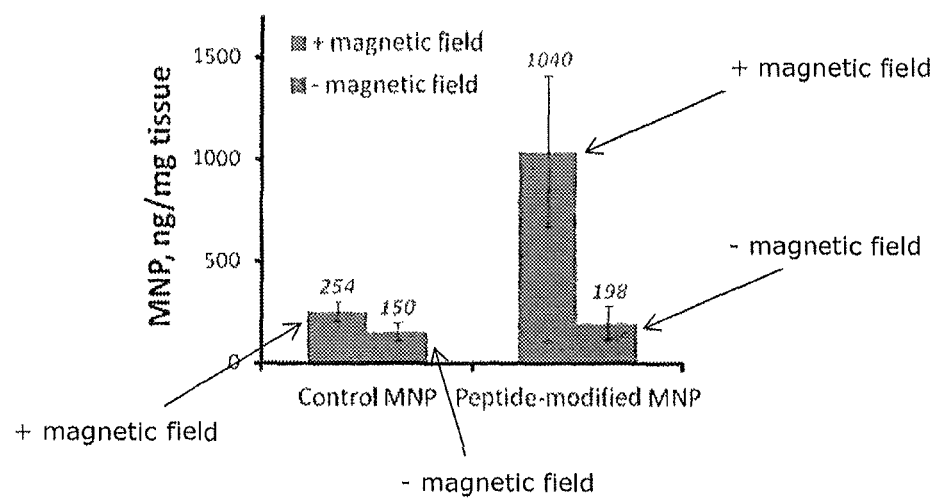
FIG. 2 shows tissue levels of peptide-modified vs. control MNP in stented arteries three days after delivery of the MNP under magnetic vs. non-magnetic conditions.

According to preferred embodiments, the therapeutic particles are produced without adversely affecting their magnetic properties, size distribution or capacity for magnetically driven cell growth inhibition. Furthermore, as described in more detail below, therapeutic particles of the present invention that were guided to stented rat carotid arteries, using a magnetizing uniform field, exhibited sustained presence at the target site at levels exceeding those achievable in the absence of affinity modification. For example, three days post-delivery, the peptide-modified magnetic nanoparticles with uniform field-controlled magnetic targeting were present in the stented arteries in an amount (ng/mg tissue) that was about four times greater than the unmodified magnetic nanoparticles with uniform field-controlled magnetic targeting (FIG. 2). The application of this dual-targeted delivery scheme (i.e., targeting by uniform field-controlled magnetic guidance and by peptide affinity modification) resulted in significantly increased amounts of magnetic nanoparticles associated with the stented arterial region three days post-treatment compared to either magnetic guidance or affinity targeting alone, and minimal redistribution of drug-loaded magnetic nanoparticles to peripheral tissues. The present invention therefore enables efficient uniform field-controlled magnetic delivery of the MNP-encapsulated drug(s), and improved retention at the target site, due to the affinity peptide modification of the MNP, which may translate into effective prevention or inhibition of in-stent restenosis.

The following example is provided to describe embodiments of the invention in greater detail and is intended to illustrate, not limit, the invention.

EXAMPLE

Methods

Polylactide-based MNP stabilized with albumin and containing 40±1% and 3.8±2% (w/w) of magnetite and paclitaxel (PTX), respectively, were formulated using a modification of the emulsification-solvent evaporation method (M. Chorny, I. Fishbein, B. B. Yellen, I. S. Alferiev, M. Bakay, S. Ganta, R. Adamo, M. Amiji, G. Friedman, and R. J. Levy. Targeting stents with local delivery of paclitaxel-loaded magnetic nanoparticles using uniform fields. *Proc Natl Acad Sci USA* 107: 8346-51 (2010)). Thiol-reactive maleimido groups were introduced on the particle surface using sulfo-SMCC and then used for covalent attachment of the peptide via its terminal cysteine residues. MNP were purified from unbound substances by magnetic decantation after each modification step. The number of thiol-reactive functions on the MNP surface accessible for peptide modification was estimated based on the binding capacity of a fluorescent model compound, 2-[(5-fluoresceinyl)aminocarbonyl]ethyl mercaptan. Cell growth inhibition studies were performed in cultured rat aortic smooth muscle cells (A10). Growth inhibition as a function of the MNP dose and exposure to a high-gradient magnetic field (32.5 T/m, 5 min) was measured fluorimetrically after 7 days in comparison to untreated cells using the Alamar Blue viability assay.

MNP biodistribution studies were performed using the rat carotid stenting model. Rat common carotid arteries were injured by a Fogarty catheter prior to deployment of a 304-grade stainless steel stent. Peptide-modified or unmodified MNP labeled with a fluorescent polylactide-BODIPY$_{564/570}$ conjugate were applied to stented arteries with or without a 1-min exposure to a uniform magnetic field generated using paired electromagnets (1,200 G). The animals were sacrificed three days post procedure, and the amounts of MNP in the stented and contralateral arteries, liver, spleen and lungs were determined fluorimetrically after tissue homogenization and polymer extraction in acetonitrile (n≥5).

Results

MNP were obtained with an average size of 250-280 nm and were shown to be able to accommodate $4\times10^4$ peptide residues per particle. The narrow size distribution, high drug loading and strong magnetic responsiveness of the particles (12.7-14.6 emu/g) in the absence of significant magnetic remnance remained unchanged following their peptide modification. In cultured rat aortic smooth muscle cells, peptide-modified MNP showed a strong magnetically driven antiproliferative effect (50% and 75% growth inhibition vs. untreated cells at the MNP doses corresponding to 5 and 20 ng PTX/well, respectively).

Three days post-delivery, tissue weight-normalized amounts of MNP determined in stented arteries were 1040±287, 254±102 and 198±81 ng/mg tissue for affinity peptide-modified MNP delivered with or without uniform field-controlled magnetic targeting and for magnetically targeted unmodified MNP, respectively (FIG. 2). The amounts of MNP detected in the liver, spleen, lung and contralateral arteries did not exceed 12 ng/mg tissue in all animal groups, suggesting that local delivery of PTX-loaded MNP to stented blood vessels is achievable with minimal carrier distribution to peripheral tissues.

The above findings suggest that biodegradable MNP formulated with antiproliferative agents, and post-modified with a fibrin-avid peptide, enable efficient and site-specific drug delivery to stented arteries when applied in combination with a magnetizing uniform field, and address the potential issue of rapid particle redistribution from the target site upon magnetic field removal. The improved retention of the drug-loaded nanoparticles in the injured artery, achievable via surface modification with fibrin-avid peptides, is expected to translate into higher therapeutic efficacy of targeted antirestenotic strategies, particularly in comparison to unmodified control MNP.

Although the present invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the appended claims.

What is claimed is:

1. A therapeutic particle comprising: a particle comprising one or more therapeutic agents, wherein one or more fibrin-avid peptide variants are attached to the surface of the particle, and wherein the one or more fibrin-avid peptide variants have the amino acid sequence selected from the group consisting of SEQ ID NO:5, SEQ ID NO:6, SEQ ID NO:7, SEQ ID NO:8, and SEQ ID NO:9.

2. The therapeutic particle of claim 1, wherein the one or more therapeutic agents comprise one or more anti-proliferative agents.

3. The therapeutic particle of claim 2, wherein the one or more anti-proliferative agents comprise paclitaxel.

4. The therapeutic particle of claim 1, wherein one or more crosslinking agents are attached to the surface of the particle, and the one or more fibrin-avid peptide variants are attached to the one or more crosslinking agents.

5. The therapeutic particle of claim 1, wherein the one or more fibrin-avid peptide variants are cysteinated variants of a fibrin-avid peptide.

6. The therapeutic particle of claim 1, wherein the one or more fibrin-avid peptide variants have the amino acid sequence of SEQ ID NO:9.

7. The therapeutic particle of claim 1, wherein the particle is a polylactide-based magnetic nanoparticle.

8. The therapeutic particle of claim 1, wherein the particle comprises one or more magnetic elements selected from the group consisting of iron, nickel, cobalt, and combinations thereof.

9. The therapeutic particle of claim 1, wherein the particle comprises magnetite.

10. The therapeutic particle of claim 1, wherein the particle is a nanoparticle having a diameter of between about 100 nm to about 500 nm.

11. The therapeutic particle of claim 1, wherein the particle is a nanoparticle having a diameter of between about 150 nm to about 350 nm.

12. The therapeutic particle of claim 1, wherein the particle is a nanoparticle having a diameter of between about 250 nm to about 280 nm.

13. The therapeutic particle of claim 1, wherein between about 10,000 to about 90,000 of the fibrin-avid peptide variants are attached to the surface of the particle.

14. The therapeutic particle of claim 1, wherein between about 30,000 to about 50,000 of the fibrin-avid peptide variants are attached to the surface of the particle.

15. A method for targeting a therapeutic agent toward a device in a subject, comprising the steps of: administering to the subject one or more therapeutic particles of claim 1.

16. The method of claim 15, wherein the one or more therapeutic agents comprise one or more anti-proliferative agents.

17. The method of claim 16, wherein the one or more anti-proliferative agents comprise paclitaxel.

18. The method of claim 15, wherein the one or more fibrin-avid peptide variants are cysteinated variants of a fibrin-avid peptide.

19. The method of claim 15, wherein the nanoparticles have an average diameter of between about 100 nm to about 500 nm.

20. The method of claim 15, wherein the nanoparticles have an average diameter of between about 200 nm to about 300 nm.

21. The method of claim 15, wherein the device is a stent.

22. The method of claim 15, comprising using a pair of electromagnets to generate a magnetic field and guide the therapeutic particles toward the device.

23. The method of claim 15, wherein the therapeutic particles comprise a therapeutically effective amount of the one or more therapeutic agents to provide an anti-proliferative effect to stented arteries.

24. The method of claim 15, wherein the therapeutic particles comprise a therapeutically effective amount of the one or more therapeutic agents to inhibit in-stent restenosis.

25. The method of claim 15, wherein each particle is a magnetic nanoparticle, the method further comprising the step of generating a magnetic field, wherein the magnetic field generates a magnetic field gradient that targets the magnetic nanoparticles toward the device.

26. A method for making a therapeutic particle comprising: attaching one or more fibrin-avid peptide variants to the surface of a particle comprising one or more therapeutic agents to prepare the therapeutic particle of claim 1.

27. The method of claim 26 further comprising using an emulsification-solvent evaporation method to make the particle.

28. The method of claim 26 further comprising attaching one or more crosslinking agents to the surface of the particle.

29. The method of claim 28, wherein the one or more crosslinking agents comprise thiol reactive functions.

30. The method of claim 28, wherein the one or more crosslinking agents comprise thiol reactive maleimido functions.

31. The method of claim 28, wherein the one or more crosslinking agents comprise sulfo-SMCC.

32. The method of claim 28 further comprising attaching the one or more fibrin-avid peptide variants to the one or more crosslinking agents.

33. The method of claim 32 comprising attaching terminal cysteine residues of the fibrin-avid peptide variants to thiol-reactive functions on the crosslinking agent.

* * * * *

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Fibrin-Avid Peptide Variant

<400> SEQUENCE: 1

Gly Pro Arg Pro
1

<210> SEQ ID NO 2
<211> LENGTH: 5
<212> TYPE: PRT
<213> ORGANISM: Artificial Sequence
<220> FEATURE:
<223> OTHER INFORMATION: Fibrin-Avid Peptide Variant

<400> SEQUENCE: 2

Gly Pro Arg Pro Pro
1               5

<210> SEQ ID NO 3
<211> LENGTH: 54
<212> TYPE: PRT
<213> ORGANISM: Artificial Sequence
<220> FEATURE:
<223> OTHER INFORMATION: Fibrin-Avid Peptide Variant
<220> FEATURE:
<221> NAME/KEY: MISC_FEATURE
<222> LOCATION: (5)..(54)
<223> OTHER INFORMATION: Xaa at positions 5-54 may be any naturally-
      occurring or artificial amino acid and up to 49 of them may be
      absent

<400> SEQUENCE: 3
```

Gly Pro Arg Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa
    50

<210> SEQ ID NO 4
<211> LENGTH: 55
<212> TYPE: PRT
<213> ORGANISM: Artificial Sequence
<220> FEATURE:
<223> OTHER INFORMATION: Fibrin-Avid Peptide Variant
<220> FEATURE:
<221> NAME/KEY: MISC_FEATURE
<222> LOCATION: (6)..(55)
<223> OTHER INFORMATION: Xaa at positions 6-55 may be any naturally-
      occurring or artificial amino acid and up to 49 of them may be
      absent

<400> SEQUENCE: 4

Gly Pro Arg Pro Pro Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa
    50                  55

<210> SEQ ID NO 5
<211> LENGTH: 55
<212> TYPE: PRT
<213> ORGANISM: Artificial Sequence
<220> FEATURE:
<223> OTHER INFORMATION: Fibrin-Avid Peptide Variant
<220> FEATURE:
<221> NAME/KEY: MISC_FEATURE
<222> LOCATION: (5)..(54)
<223> OTHER INFORMATION: Xaa at positions 5-54 may be any naturally-
      occurring or artificial amino acid and up to fifty of them may be
      absent

<400> SEQUENCE: 5

Gly Pro Arg Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Cys
    50                  55

<210> SEQ ID NO 6
<211> LENGTH: 56
<212> TYPE: PRT
<213> ORGANISM: Artificial Sequence
<220> FEATURE:
<223> OTHER INFORMATION: Fibrin-Avid Peptide Variant
<220> FEATURE:
<221> NAME/KEY: MISC_FEATURE
<222> LOCATION: (6)..(55)
<223> OTHER INFORMATION: Xaa at positions 6-55 may be any naturally-occurring or artificial amino acid and up to fifty of them may
be absent

<400> SEQUENCE: 6

Gly Pro Arg Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Cys
    50                  55

<210> SEQ ID NO 7
<211> LENGTH: 55
<212> TYPE: PRT
<213> ORGANISM: Artificial Sequence
<220> FEATURE:
<223> OTHER INFORMATION: Fibrin-Avid Peptide Variant
<220> FEATURE:
<221> NAME/KEY: MISC_FEATURE
<222> LOCATION: (5)..(54)
<223> OTHER INFORMATION: Xaa at positions 5-54 are Gly and up to 49
      of them may be absent

<400> SEQUENCE: 7

Gly Pro Arg Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Cys
    50                  55

<210> SEQ ID NO 8
<211> LENGTH: 56
<212> TYPE: PRT
<213> ORGANISM: Artificial Sequence
<220> FEATURE:
<223> OTHER INFORMATION: Fibrin-Avid Peptide Variant
<220> FEATURE:
<221> NAME/KEY: MISC_FEATURE
<222> LOCATION: (6)..(55)
<223> OTHER INFORMATION: Xaa at positions 6-55 are Gly and up to 49 of
      them may be absent

<400> SEQUENCE: 8

Gly Pro Arg Pro Pro Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Cys
    50                  55

<210> SEQ ID NO 9
<211> LENGTH: 9
<212> TYPE: PRT
<213> ORGANISM: Artificial Sequence
<220> FEATURE:
<223> OTHER INFORMATION: Fibrin-Avid Peptide Variant

```
<400> SEQUENCE: 9

Gly Pro Arg Pro Pro Gly Gly Gly Cys
1               5
```